United States Patent
Thomas

(10) Patent No.: US 9,487,832 B2
(45) Date of Patent: Nov. 8, 2016

(54) SELECTIVE DETECTION OF NEISSERIA MENINGITIDIS

(75) Inventor: Jennifer Thomas, Atlanta, GA (US)

(73) Assignee: The Government of the United States of America, as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 314 days.

(21) Appl. No.: 13/816,903

(22) PCT Filed: Oct. 11, 2011

(86) PCT No.: PCT/US2011/055784
§ 371 (c)(1),
(2), (4) Date: Jun. 13, 2013

(87) PCT Pub. No.: WO2012/048339
PCT Pub. Date: Apr. 12, 2012

(65) Prior Publication Data
US 2014/0178868 A1    Jun. 26, 2014

Related U.S. Application Data

(60) Provisional application No. 61/391,493, filed on Oct. 8, 2010.

(51) Int. Cl.
*C12Q 1/68* (2006.01)
(52) U.S. Cl.
CPC ................................... *C12Q 1/689* (2013.01)
(58) Field of Classification Search
None
See application file for complete search history.

(56) References Cited

U.S. PATENT DOCUMENTS 5,747,252 A    5/1998    Yang et al.

FOREIGN PATENT DOCUMENTS

WO    2009063243 A2    5/2009

OTHER PUBLICATIONS

Kroll et al. Microbiology 141: 2271-2279 (1995).*
Corless et al. Journal of Clinical Microbiology, 2001, vol. 39, pp. 1553-1558.*
Dolan-Livengood et al. The Journal of Infectious Diseases, 2003, vol. 187, pp. 1616-1628.*
Sloan, L. Clinical Microbiology Newsletter, 2007, vol. 29, pp. 87-95.*
Kroll et al. Proceedings of the National Academy of Sciences USA, 1998, vol. 95, pp. 12381-12385.*
Savelkoul et al. Journal of Microbiological Methods, 2006, vol. 66, pp. 177-180.*
Geens et al. Veterinary Research, 2005, vol. 36, pp. 787-797.*
Stevenson et al. Applied Microbiology and Biotechnology, 2007, vol. 75, pp. 165-174.*
Seward, R.J., "Evaluation of a PCR-immunoassay technique for detection of Neisseria meningitidis in cerebrospinal fluid and peripheral blood," J. Med. Microbiol., vol. 49, No. 5, pp. 451-456, May 2000.
Yazdankhah, S. P., "Neisseria meningitidis: an overview of the carriage state," J. Med. Microbiol., vol. 53, Pt. 9, pp. 821-832, Sep. 2004.
Dolan, T. J., "sodC-based real-time PCR for detection of Neisseria meningitidis," PLoS One, vol. 6, No. 5, e19361, May 5, 2011.
Wilks, K.E. et al., "Periplasmic Superoxide Dismutase in Meningococcal Pathogenicity, Infection and Immunity," American Society for Macrobiology, 66(1): 213-217, Jan. 1, 1998.
Seib, K.L., "Defenses against Oxidative Stress in Neisseria gonorrhoeae and Neisseria meningitidis: Distinctive Systems for Different Lifestyles," The Journal of Infectious Diseases, 190(1): 136-147, Jul. 1, 2004.
Zhu, P. et al., "Nonencapsulated Neisseria meningitidis Strain produces Amylopectin from Sucrose: Altering the Concept for Differntiation between N. Meningitidis and N. polysaccharea," Journal of Clinical Microbiology, 41(1): 273-278, Jan. 1, 2003.
Taha, M., "Simultaneous Approach for Nonculture PCR-Based Indentification and Serogroup Prediction of Neisseria meningitidis," Journal of Clinical Microbiology, 38(2): 855-857, Jan. 1, 2000.
Sanjay, M.K. et al., Indian J Medical Research (2010) 131: 565-570.

* cited by examiner

*Primary Examiner* — Angela M Bertagna
(74) *Attorney, Agent, or Firm* — Dinsmore & Shohl LLP; Weston R. Gould

(57)    ABSTRACT

A process for detecting *Neisseria meningitidis* nucleic acid in a sample is provided including producing an amplification product by amplifying *Neisseria meningitidis* nucleotide sequence of the sodC gene or mRNA using a forward primer of SEQ ID NO: 1, and a reverse primer of SEQ ID NO: 2, and detecting the amplification product to detect *Neisseria meningitidis* in the sample. Also provided are reagents and methods for detecting and distinguishing *Neisseria meningitidis* from other infectious agents. A kit is provided for detecting and quantifying *Neisseria meningitidis* in a sample.

11 Claims, No Drawings

SELECTIVE DETECTION OF NEISSERIA MENINGITIDIS

CROSS REFERENCE TO RELATED APPLICATIONS

This application depends from and claims priority to U.S. Provisional Patent Application No. 61/391,493 filed Oct. 8, 2010, the entire contents of which are incorporated herein by reference.

GOVERNMENT INTEREST

The invention described herein may be manufactured, used, and licensed by or for the United States Government.

FIELD OF THE INVENTION

This invention relates generally to processes for detection of foreign organisms in fluid samples. More specifically, the invention relates to selective detection of *Neisseria meningitidis* in biological or other fluid media. Processes are described for rapid and sensitive detection of *N. meningitidis* in biological samples and quantification thereof. Diagnostic kits are provided for detection of *N. meningitidis* in a clinical, laboratory, or field setting.

BACKGROUND OF THE INVENTION

*Neisseria meningitidis* (Nm) is the etiologic agent of epidemic bacterial meningitis and rapidly fatal sepsis throughout the world. Rapid detection of Nm infection and early treatment initiation are essential to positive outcomes in patients. Techniques commonly employed for the identification of Nm include biochemical tests, slide agglutination serogrouping (SASG), and the polymerase chain reaction (PCR) Coreless, C E, et al., *J Clin Microbiol*, 2001; 39:1553-8; Jordens, J. Z., and J. E. Heckels, *J Med Microbiol*, 2005; 54:463-6; Mothershed, E. A. et al., *J Clin Microbiol*, 2004; 42:320-8; Taha, M. K., *J Clin Microbiol*, 2000; 38:855-7. The chromogenic tests and SASG can be subjective, which often complicates species identification.

ctrA may be the most frequently targeted gene to detect Nm using PCR. Taha, M. et al., *J Clin Microbiol*, 2005; 43:144-9. However, the capsule locus, including ctrA, is subject to rearrangement, and 16% or more of carried meningococci have been shown to lack ctrA altogether. Invasive NG meningococci can undergo similar rearrangements of the capsule region (J. Dolan Thomas, unpublished data), although these events may be less common than in carnage isolates.

Thus, there is a need for compositions and methods to detect of meningococci, especially of carriage isolates that may be ctrA-negative and NG.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Processes and materials are provided for the detection of the presence or absence of *Neisseria meningitidis* in a sample. A process illustratively includes producing an amplification product by amplifying a *Neisseria meningitidis* nucleotide sequence using a forward primer that hybridizes to a region within the sodC gene of *Neisseria meningitidis*, a reverse primer that hybridizes to a region within the sodC gene of *Neisseria meningitidis*, and optionally a probe that hybridizes to a region within the sodC gene of *Neisseria meningitidis* under conditions suitable for a polymerase chain reaction; and detecting the amplification product to detect the *Neisseria meningitidis* in said sample. A forward primer optionally includes SEQ ID NO: 1. A reverse primer optionally includes SEQ ID NO: 2. A probe is optionally labeled. A probe optionally includes SEQ ID NO: 3.

The probe is hybridized to an amplification product under conditions suitable for a polymerase chain reaction so as to produce a first detection signal. The detection of an amplification optionally diagnoses *Neisseria meningitidis* infection in a subject from which the sample is derived. The absence of an amplification product or a first amplification signal optionally diagnoses the absence of *Neisseria meningitidis* infection in a subject from which the sample is derived.

One or more controls are optionally analyzed. Optionally, the first detection signal is compared to a second detection signal, wherein the second detection signal results from detection of a complementary amplification product produced from a control sample. Optionally, the complementary amplification product is generated by PCR amplification of a purified *Neisseria meningitidis*, or portion thereof, or from a nucleic acid calibrator. A second detection signal, or a third detection signal derived from a nucleic acid calibrator are optionally generated in parallel with the first detection signal. A nucleic acid calibrator is optionally extracted in parallel to said sample. A nucleic acid calibrator is optionally a known amount of *Neisseria meningitidis* sodC nucleic acid sequence and a known amount of a medium similar to the sample.

Also provided are kits for detecting *Neisseria meningitidis* infection including a first forward primer with sequence SEQ ID NO: 1, a first reverse primer with SEQ ID NO: 2, and a probe. The probe optionally has the sequence SEQ ID NO: 3.

Also provided are isolated oligonucleotides suitable for use in detecting the presence or absence of a sodC nucleic acid sequence in a sample. An oligonucleotide optionally is or includes the sequence of SEQ ID NO: 1, SEQ ID NO: 2, or SEQ ID NO: 3.

DETAILED DESCRIPTION OF EMBODIMENTS OF THE INVENTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the process is described as an order of individual steps or using specific materials, it is appreciated that described steps or materials may be interchangeable such that the description of the invention includes multiple parts or steps arranged in many ways as is readily appreciated by one of skill in the art.

The invention has utility for the detection of *Neisseria meningitidis* (Nm) in a sample. As it is necessary to detect small numbers of Nm in clinical specimens due to bacterial loads in cerebrospinal fluid (CSF) of patients ranging from $3 \times 10^1$ to $4 \times 10^9$ CFU/mL, sensitive techniques such as PCR may provide a more reliable diagnostic than other currently employed assay systems. Unlike chromogenic tests and SASG, PCR does not require viable bacteria and can be used to identify and characterize even nongroupable (NG) meningococci. Real-time PCR (rt-PCR) of the ctrA gene is capable of detecting as few as 8 meningococcal genomes per reaction (17, 26) and results are obtained within 2.5 hours. Unfortunately, prior attempts at detection of Nm using PCR techniques are incapable of detecting all strains due to selection pressure resulting in false negatives in samples. Among the thousands of possible candidates, the inventors discovered that the sodC gene is less susceptible to mutation due to bacterial selection pressures and is present in all strains tested. Further, sodC presents a selective target as it is not present in other *Neisseria* spp. Thus, the invention has superior utility over prior methods of detection of Nm in samples and diagnosis of bacterial meningitis in a subject.

The [Cu, Zn]-cofactored superoxide dismutase gene, sodC, is located 1.23 Mb from the capsule locus in the 2.27-Mb Nm serogroup B strain MC58 genome and encodes the virulence factor Cu, Zn Sod. Cu, Zn Sod is a periplasmic enzyme, making it theoretically less susceptible to antigenic variation due to selective pressure than a cell-surface exposed molecule. sodC is believed to have been acquired by Nm via horizontal transfer from *Haemophilus influenzae* (Hi), but the inventors find no cross-reactivity between Nm and Hi using the inventive sodC assay.

Compositions and methods are provided for the sensitive detection of Nm in samples, such as biological or environmental samples, using techniques involving PCR. Primers are provided that amplify regions of sodC from Nm with high specificity and broad Nm recognition that are subsequently detectable, optionally by sensitive detection systems.

In some embodiments, sodC is used to define a consensus sequence for *Neisseria meningitidis* sodC obtained from meningococcal strains Z2491 (nts 1521721-1522258), FAM18, and MC58 (respective GenBank accession numbers AL157959.1, AM421808.1, and AE002098.2).

The following definitional terms are used throughout the specification without regard to placement relative to these terms.

As used herein, the term "variant" defines either a naturally occurring genetic mutant of the sodC gene or gene products of Nm, or a recombinantly prepared variation of the sodC gene or gene products of Nm, each of which contain one or more mutations in its sodC gene compared to the sequence of one or more of Genbank accession nos. AL157959.1, AM421808.1, or AE002098.2. The term "variant" may also refer to either a naturally occurring variation of a given peptide or a recombinantly prepared variation of a given peptide or protein in which one or more amino acid residues have been modified by amino acid substitution, addition, or deletion.

As used herein, the term "analog" in the context of a non-proteinaceous analog defines a second organic or inorganic molecule that possesses a similar or identical function as a first organic or inorganic molecule and is structurally similar to the first organic or inorganic molecule.

As used herein, the term "derivative" in the context of a non-proteinaceous derivative defines a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated. A derivative also defined as a degenerate base mimicking a C/T mix such as that from Glen Research Corporation, Sterling, Va., illustratively LNA-dA or LNA-dT, or other nucleotide modification known in the art or otherwise.

As used herein, the term "mutant" defines the presence of mutations in the nucleotide sequence of an organism as compared to a wild-type organism. A mutant is a variant.

The description of a target nucleic acid molecule is presented herein as sodC. In some embodiments, sodC specifically includes variants, analogues, derivatives, and mutants of sodC. In some embodiments, sodC specifically excludes variants, analogues, derivatives, and mutants of sodC and is, therefore, directed to only sequences of sodC found in nature.

A "purified" nucleic acid molecule is one that is separated from other nucleic acid molecules that are present in the natural source of the nucleic acid molecule and is often substantially free of other cellular material, or culture medium when produced by recombinant techniques, or substantially free of chemical precursors or other chemicals when chemically synthesized. This term is exclusive of a nucleic acid that is a member of a library that has not been purified away from other library clones containing other nucleic acid molecules.

As used herein, the term "hybridizes under stringent conditions" describes conditions for hybridization and washing under which nucleotide sequences having at least 30%, 35%, 40%, 45%, 50%, 55%, 60%, 65%, 70%, 75%, 80%, 85%, 90%, 95%, or more, base pair matches to each other typically remain hybridized to each other. Illustrative hybridization conditions are described in, for example but not limited to, Current Protocols in Molecular Biology, John Wiley & Sons, N.Y. (1989), 6.3.1 6.3.6.; Basic Methods in Molecular Biology, Elsevier Science Publishing Co., Inc., N.Y. (1986), pp. 75 78, and 84 87; and Molecular Cloning, Cold Spring Harbor Laboratory, N.Y. (1982), pp. 387 389, and are well known to those skilled in the art. A non-limiting example of stringent hybridization conditions is hybridization in 6× sodium chloride/sodium citrate (SSC), 0.5% SDS at about 60° C. followed by one or more washes in 2×SSC, 0.5% SDS at room temperature. Another non-limiting example of stringent hybridization conditions is hybridization in 6×SSC at about 45° C. followed by one or more washes in 0.2×SSC, 0.1% SDS at 50 to 65° C. Other stringent hybridization conditions will be evident to one of ordinary skill in the art based on general knowledge in the art as well as this specification.

An "isolated" or "purified" nucleotide or oligonucleotide sequence is substantially free of cellular material or other contaminating proteins from the cell or tissue source from which the nucleotide is derived, or is substantially free of chemical precursors or other chemicals when chemically synthesized. The language "substantially free of cellular material" includes preparations of a nucleotide/oligonucleotide in which the nucleotide/oligonucleotide is separated from cellular components of the cells from which it is isolated or produced. Thus, a nucleotide/oligonucleotide that is substantially free of cellular material includes preparations of the nucleotide having less than about 30%, 20%, 10%, 5%, 2.5%, or 1%, (by dry weight) of contaminating material. When nucleotide/oligonucleotide is produced by chemical synthesis, it is optionally substantially free of chemical precursors or other chemicals, i.e., it is separated from chemical precursors or other chemicals which are involved in the synthesis of the molecule. Accordingly, such preparations of the nucleotide/oligonucleotide have less than about 30%, 20%, 10%, 5% (by dry weight) of chemical precursors or compounds other than the nucleotide/oligonucleotide of interest. In some embodiments of the present invention, a nucleotide/oligonucleotide is isolated or purified.

As used herein, the term "sample" is a portion of a larger source. A sample is optionally a solid, gaseous, or fluidic sample. A sample is illustratively an environmental or biological sample. An environmental sample is illustratively, but not limited to, water, sewage, soil, or air. A "biological sample" is as sample obtained from a biological organism, a tissue, cell, cell culture medium, or any medium suitable for mimicking biological conditions. Non-limiting examples include, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions, throat or nasal materials. In some embodiments, target agents are contained in: CSF; serum; whole blood; throat fluid; nasopharyngeal fluid; or other respiratory fluid.

As used herein, the term "medium" refers to any liquid or fluid sample in the presence or absence of a bacterium. A medium is illustratively a solid sample that has been suspended, solubilized, or otherwise combined with fluid to form a fluidic sample. Non-limiting examples include buffered saline solution, cell culture medium, acetonitrile, trifluoroacetic acid, combinations thereof, or any other fluid recognized in the art as suitable for combination with bacteria or other cells, or for dilution of a biological sample or amplification product for analysis.

To determine the percent identity of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In some embodiments, the two sequences are the same length.

The determination of percent identity between two sequences can also be accomplished using a mathematical algorithm. A non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described herein or otherwise known in the art, with or without allowing gaps. In calculating percent identity, typically only exact matches are counted.

As used herein, the terms "subject" and "patient" are synonymous and refer to a human or non-human animal, optionally a mammal including a human, a non-primate such as cows, pigs, horses, goats, sheep, cats, dogs, avian species and rodents; and a non-human primate such as monkeys, chimpanzees, and apes; and a human, also optionally denoted specifically as a "human subject".

Processes are described that provide a rapid, specific, and sensitive assay for detection of Nm in a sample by amplifying one or more nucleotide sequences of the sodC gene by processes similar to the polymerase chain reaction (PCR). Processes are similarly provided for diagnosing the presence or absence of Nm infection in a subject. The presence of Nm detected in a sample from the subject diagnoses or confirms a prior diagnosis of infection of the subject by Nm. The absence of Nm in a sample from a subject diagnoses the absence of an infection of the subject by Nm.

An oligonucleotide forward primer with a nucleotide sequence complementary to a unique sequence in a sodC nucleotide sequence corresponding to the sodC sequence in one or more Nm is hybridized to its complementary sequence and extended. A nucleotide sequence is complementary if it hybridizes under stringent conditions. Similarly, a reverse oligonucleotide primer complementary to a second strand of Nm DNA in a separate sodC region is hybridized and extended. This system allows for amplification of specific gene sequences and is suitable for simultaneous or sequential detection systems. It is appreciated that while the description is generally directed to sequences of the sodC gene, or a Nm consensus sequence thereof, that detection of mRNA encoding at least a portion of SodC protein is equally detectable by the processes and compositions of the inventions.

The present invention relates to the use of the sequence information of Nm for diagnostic processes. In particular, the present invention provides a process for detecting the presence or absence of nucleic acid molecules of Nm, natural or artificial variants, analogs, or derivatives thereof, in a sample. In some embodiments, processes involve obtaining a biological sample from one or more of various sources and contacting the sample with a compound or an agent capable of detecting a nucleic acid sequence of sodC, natural or artificial variants, analogs, or derivatives thereof, such that the presence of Nm, natural or artificial variants, analogs, or derivatives thereof, is detected in the sample. Optionally, infection by *Neisseria meningitidis* is diagnosed by positively detecting one or more Nm in the sample. In some embodiments, the presence of Nm, natural or artificial variants, analogs, or derivatives thereof, is detected in the sample using a PCR reaction or real-time polymerase chain reaction (RT-PCR) including primers that are constructed based on a partial nucleotide sequence of the Nm organism. As sodC is present in both Nm and *H. influenzae*, simple identification of primers such as by a software program alone is insufficient for use in an inventive assay. Primers must be designed to amplify sodC from the greatest number of Nm strains while not amplifying sodC from *H. influenzae* so as to prevent false positives. In a non-limiting embodiment, a forward primer designed to be successful for selective amplification in a PCR based assay such as in a RT-PCR process is illustratively 5'-GCACACTTAGGTGATTTAC-CTGCAT-3' (SEQ ID NO: 1). In some embodiments, a reverse primer designed to be successful for selective amplification in a PCR based assay such as in a RT-PCR process is illustratively 5'-CCACCCGTGTGGATCATAATAGA-3' (SEQ ID NO: 2). In some embodiments, the primers used in a process are the nucleic acid sequences of SEQ ID NOs:1 and 2. As used herein, the term "amplify" is defined as producing one or more copies of a target molecule, or a complement thereof. A nucleic acid such as DNA or RNA is amplified to produce one or more amplification products. Illustratively, a forward primer and an optional reverse primer are contacted with a target under conditions suitable for a polymerase chain reaction to produce an amplification product.

An agent for detecting *Neisseria meningitidis* nucleic acid sequences is a labeled nucleic acid probe capable of hybridizing to a portion of the sodC gene, mRNA, or amplification products derived therefrom. In some embodiments, the nucleic acid probe is a nucleic acid molecule of the nucleic acid sequence of 5'-CATGATGGCACAGCAACAAATC-CTGTTT-3' (SEQ ID NO: 3), which sufficiently specifically hybridizes under stringent conditions to a *Neisseria meningitidis* nucleic acid sequence. A probe is optionally labeled with a fluorescent molecule such as a fluorescein (FAM) molecule and optionally a quencher such as the black hole quencher BHQ1.

Primers are optionally used for the sequencing of the sodC gene of an Nm. Illustratively, primers for PCR include a forward primer 5'-CCTTATTAGCACTAGCGGTTAG-3' (SEQ ID NO: 4 and a reverse primer 5'-CCGGTCATCTTT-TATGCTCCAA-3' (SEQ ID NO: 5).

Processes optionally involve a real-time PCR assay (RT-PCR), optionally, a real-time quantitative PCR assay. In some embodiments, the PCR assay is a TaqMan assay (Holland et al., PNAS 88(16):7276 (1991)). It is appreciated that the processes are amenable to performance on other RT-PCR systems and protocols that use alternative reagents illustratively including, but not limited to Molecular Beacons probes, Scorpion probes, multiple reporters for multiplex PCR, combinations thereof, or other DNA detection systems.

The assays are performed on an instrument designed to perform such assays, for example those available from Applied Biosystems (Foster City, Calif.). In some embodiments, a real-time quantitative PCR assay is used to detect the presence of Nm, natural or artificial variants, analogs, or derivatives thereof, in a sample by subjecting the Nm nucleic acid from the sample to PCR reactions using specific primers, and detecting the amplified product using a probe. In some embodiments, the probe is a TaqMan probe which consists of an oligonucleotide with a 5'-reporter dye and a 3'-quencher dye.

A fluorescent reporter dye, such as FAM dye (illustratively 6-carboxyfluorescein), is covalently linked, optionally to the 5' end of the oligonucleotide probe. Other dyes illustratively include TAMRA, AlexaFluor dyes such as AlexaFluor 495 or 590, Cascade Blue, Marina Blue, Pacific Blue, Oregon Green, Rhodamine, Fluoroscein, TET, HEX, Cy5, Cy3, and Tetramethylrhodamine. A reporter is optionally quenched by a dye at the 3' end or other non-fluorescent quencher. Quenching molecules are optionally suitably matched to the fluorescence maximum of the dye. Any suitable fluorescent probe for use in RT-PCR detection systems is illustratively operable in the instant invention. Similarly, any quenching molecule for use in RT-PCR systems is illustratively operable. In some embodiments, a 6-carboxyfluorescein reporter dye is present at the 5'-end and matched to BLACK HOLE QUENCHER (BHQ1, Biosearch Technologies, Inc., Novato, Calif.) The fluorescence signals from these reactions are captured at the end of extension steps as PCR product is generated over a range of the thermal cycles, thereby allowing the quantitative determination of the bacterial load in the sample based on an amplification plot.

The *Neisseria meningitidis* nucleic acid sequences are optionally amplified before or simultaneous with being detected. The term "amplified" defines the process of making multiple copies of the nucleic acid from a single or lower copy number of nucleic acid sequence molecule. The amplification of nucleic acid sequences is carried out in vitro by biochemical processes known to those of skill in the art, illustratively by PCR techniques. The amplification agent may be any compound or system that will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, AmpliTaq Gold DNA Polymerase from Applied Biosystems, other available DNA polymerases, reverse transcriptase (preferably iScript RNase H+ reverse transcriptase), ligase, and other enzymes, including heat-stable enzymes (i.e., those enzymes that perform primer extension after being subjected to temperatures sufficiently elevated to cause denaturation). In some embodiments, the enzyme is hot-start iTaq DNA polymerase from Bio-rad (Hercules, Calif.). Suitable enzymes will facilitate combination of the nucleotides in the proper manner to form the primer extension products that are complementary to each mutant nucleotide strand. Generally, the synthesis is initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same or similar processes as described herein. In any event, the processes of the invention are not to be limited to the embodiments of amplification described herein.

One process of in vitro amplification, which optionally is used according to this invention, is the polymerase chain reaction (PCR) described in U.S. Pat. Nos. 4,683,202 and 4,683,195. The term "polymerase chain reaction" refers to a process for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many polymerase chain processes are known to those of skill in the art and may be used in the process of the invention. For example, DNA is subjected to 30 to 35 cycles of amplification in a thermocycler as follows: 2 minutes at 50° C., 10 minutes at 95° C., and then 50×(15 seconds at 95° C. plus 1 minute at 60° C.).

The primers for use in amplifying the mRNA or genomic DNA of Nm may be prepared using any suitable process, such as conventional phosphotriester and phosphodiester processes or automated embodiments thereof so long as the primers are capable of hybridizing to the nucleic acid sequences of interest. One process for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the process of the invention are complementary to each strand of nucleotide sequence to be amplified. The term "complementary" means that the primers hybridize with their respective strands under conditions, which allow the agent for polymerization to function, such as stringent hybridization conditions. In other words, the primers that are complementary to the flanking sequences hybridize with the flanking sequences and permit amplification of the nucleotide sequence. Optionally, the 3' terminus of the primer that is extended is perfectly (100%) base paired with the complementary flanking strand. Probes optionally possess nucleotide sequences complementary to one or more strands of the sodC gene of Nm. Optionally, primers contain the nucleotide sequences of SEQ ID NOs: 1 and 2. It is appreciated that the complements of SEQ ID NOs: 1 and 2 are similarly suitable for use in the instant inventions. It is further appreciated that oligonucleotide sequences that hybridize with SEQ ID NOs 1 or 2 are also similarly suitable. Finally, multiple positions are available for hybridization on the sodC gene and will be also suitable hybridization with a probe when used with the proper forward and reverse primers.

Those of ordinary skill in the art will know of various amplification processes that can also be utilized to increase the copy number of target Nm nucleic acid sequence. The nucleic acid sequences detected in the process of the invention are optionally further evaluated, detected, cloned, sequenced, and the like, either in solution or after binding to a solid support, by any process usually applied to the detection of a specific nucleic acid sequence such as another polymerase chain reaction, oligomer restriction (Saiki et al., BioTechnology 3:1008 1012 (1985)), allele-specific oligonucleotide (ASO) probe analysis (Conner et al., PNAS 80: 278 (1983)), oligonucleotide ligation assays (OLAs) (Landegren et al., Science 241:1077 (1988)), RNase Protection Assay, among others. Molecular techniques for DNA analysis have been reviewed (Landegren et al, Science 242:229 237 (1988)). Following DNA amplification, the reaction product may be detected by Southern blot analysis, with or without using radioactive probes. In such a process, for example, a small sample of DNA containing the nucleic acid sequence obtained from the tissue or subject is amplified, and analyzed via a Southern blotting technique. The use of non-radioactive probes or labels is facilitated by the high level of the amplified signal. In some embodiments of the invention, one nucleoside triphosphate is radioactively labeled, thereby allowing direct visualization of the amplification product by autoradiography. In some embodiments, amplification primers are fluorescently labeled and run through an electrophoresis system. Visualization of amplified products is by light detection followed by computer assisted graphic display, without a radioactive signal.

Other methods of detection amplified oligonucleotide illustratively include gel electrophoresis, mass spectrometry, liquid chromatography, fluorescence, luminescence, gel mobility shift assay, fluorescence resonance energy transfer, nucleotide sequencing, enzyme-linked immunoadsorbent assay, affinity chromatography, other chromatography methods, immunoenzymatic methods (Ortiz, A and Ritter, E, *Nucleic Acids Res.,* 1996; 24:3280-3281), streptavidin-conjugated enzymes, DNA branch migration (Lishanski, A, et al., *Nucleic Acids Res.,* 2000; 28(9):e42), enzyme digestion (U.S. Pat. No. 5,580,730), colorimetric methods (Lee, K., *Biotechnology Letters,* 2003; 25:1739-1742), or combinations thereof. A detection signal is produced that is related to the detection method employed, be it RT-PCR or other detection method. A test sample optionally produces a first detection signal upon amplification of a target. A control sample optionally produces a second detection signal upon amplification of a control molecule.

The term "labeled" with regard to the probe is intended to encompass direct labeling of the probe by coupling (i.e., physically linking) a detectable substance to the probe, as well as indirect labeling of the probe by reactivity with another reagent that is directly labeled. Examples of indirect labeling include detection of a probe using a fluorescently labeled antibody and end-labeling or centrally labeling of a DNA probe with biotin such that it can be detected with fluorescently labeled streptavidin. The detection methods can be used to detect RNA (particularly mRNA), genomic nucleic acid, or amplification products thereof, in a sample in vitro as well as in vivo. For example, in vitro techniques for detection of nucleic acid include northern hybridizations, in situ hybridizations, reverse transcription-PCR, real-time-PCR, and DNase protection. In vivo techniques for detection of Nm include introducing into a subject organism a labeled antibody directed against a polypeptide component or directed against a particular nucleic acid sequence of Nm. For example, the antibody can be labeled with a radioactive marker whose presence and location in the subject organism can be detected by standard imaging techniques, including autoradiography.

The size of the primers used to amplify a portion of the nucleic acid sequence of Nm is at least 5, and often 10, 15, 20, 25, 30 or more nucleotides in length, optionally any value or range between 5 and 30 nucleotides in length. Optionally, the GC ratio is above 30%, 35%, 40%, 45%, 50%, 55%, or 60% so as to prevent hair-pin structure on the primer. The amplicon is optionally of sufficient length to be detected by standard molecular biology methodologies. The forward primer is optionally shorter than the reverse primer or vice versa. Techniques for modifying the $T_m$ of either primer are operable herein. An illustrative forward primer contains LNA-dA and LNA-dT (Glen Research Corporation) so as to match $T_m$ with a corresponding alternate primer.

An inventive process uses a polymerization reaction which employs a nucleic acid polymerizing enzyme, illustratively a DNA polymerase, RNA polymerase, reverse transcriptase, or mixtures thereof. It is further appreciated that accessory proteins or molecules are present to form the replication machinery. A polymerizing enzyme is optionally a thermostable polymerase or thermodegradable polymerase. Use of thermostable polymerases is well known in the art such as Taq polymerase available from Invitrogen Corporation, Carlsbad, Calif. Thermostable polymerases allow a polymerization reaction to be initiated or shut down by changing the temperature other condition in the reaction mixture without destroying activity of the polymerase.

Accuracy of the base pairing of DNA sequence amplification is provided by the specificity of the enzyme. Error rates for Taq polymerase tend to be false base incorporation of $10^{-5}$ or less. (Johnson, *Annual Reviews of Biochemistry*, 1993: 62:685-713; Kunkel, *Journal of Biological Chemistry*, 1992; 267:18251-18254). Specific examples of thermostable polymerases illustratively include those isolated from *Thermus aquaticus, Thermus thermophilus, Pyrococcus woesei, Pyrococcus furiosus, Thermococcus litoralis* and *Thermotoga maritima*. Thermodegradable polymerases illustratively include *E. coli* DNA polymerase, the Klenow fragment of *E. coli* DNA polymerase, T4 DNA polymerase, T7 DNA polymerase and other examples known in the art. It is recognized in the art that other polymerizing enzymes are similarly suitable illustratively including *E. coli*, T7, T3, SP6 RNA polymerases and AMV, M-MLV, and HIV reverse transcriptases.

The polymerases are optionally bound to the primer. When the Nm sodC gene sequence is a single-stranded DNA molecule due to heat denaturing, the polymerase is bound at the primed end of the single-stranded nucleic acid at an origin of replication. A binding site for a suitable polymerase is optionally created by an accessory protein or by any primed single-stranded nucleic acid.

In some embodiments, detection of PCR products of sodC or sodC nucleic acid sequence is achieved by mass spectrometry. Mass spectrometry has several advantages over real-time PCR systems in that it can be used to simultaneously detect the presence of Nm and decipher mutations in target nucleic acid sequences allowing identification and monitoring of emerging strains. Further, mass spectrometers are prevalent in the clinical laboratory. Similar to fluorescence based detection systems, mass spectrometry is capable of simultaneously detecting multiple amplification products for a multiplexed and controlled approach to accurately quantifying components of biological or environmental samples.

Multiple mass spectrometry platforms are suitable for use in the invention illustratively including matrix assisted laser desorption ionization time of flight mass spectrometry (MALDI), electrospray mass spectrometry, electrospray ionization-Fourier transform ion cyclotron resonance mass spectrometry (ESI-FTICR), multi-stage mass spectrometry fragmentation analysis (MS/MS), mass spectrometry coupled with liquid chromatography such as high performance liquid chromatography mass spectrometry (HPLC) and ultra performance liquid chromatography isotope dilution tandem mass spectrometry (UPLC-ID/MS/MS), and variations thereof.

It is appreciated that numerous other detection processes are similarly suitable for measuring an amplification product by detecting a detection signal. Illustrative examples include, but are not limited to, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time PCR(RT-PCR), gel electrophoresis, or combinations thereof.

Optionally, PCR amplification products are generated using complementary forward and reverse oligonucleotide primers. In a non-limiting example, Nm genetic sequences or fragments thereof are amplified by the primer pair SEQ ID NOs: 1 and 2 that amplify a conserved sequence in the sodC gene encompassing nucleotides 351-478. The resulting amplification product is either directly detected such as by a probe, or is subsequently processed and prepared for detection by processes known in the art. It is appreciated that the complements of SEQ ID NOs: 1 and 2 are similarly suitable for use in the invention. It is further appreciated that oligonucleotide sequences that hybridize with SEQ ID NOs: 1 or 2 are also similarly suitable. Finally, multiple positions are available for hybridization on the Nm genome and in the sodC gene, gene product, or other and will be also suitable hybridization with forward and reverse primers that may or may not be used with a probe for real-time PCR.

Optionally, multiple amplification products are simultaneously produced in a PCR reaction that are then available for simultaneous detection and quantification. Thus, multiple detection signals are inherently produced or emitted that are separately and uniquely detected in one or more detection systems. It is appreciated that multiple detection signals are optionally produced in parallel. Optionally, a single biological sample is subjected to analysis for the simultaneous or sequential detection of Nm genetic sequences. It is appreciated that three or more independent or overlapping sequences are simultaneously or sequentially measured in the inventive processes. Oligonucleotide matched primers (illustratively SEQ ID NOs: 1 and 2) are simultaneously or sequentially added and the biological sample, or a portion thereof, is subjected to proper thermocycling reaction parameters. For detection by mass spectrometry, a single sample of the amplification products from each gene are simultaneously analyzed allowing for rapid and accurate determination of the presence of Nm. Optionally, analysis by real-time PCR is employed capitalizing on multiple probes with unique fluorescent signatures. Thus, each gene is detected without interference by other amplification products. This multi-target approach increases confidence in quantification and provides for additional internal control.

In some embodiments, the processes further involve optionally obtaining a control sample from a control subject, contacting a control sample, optionally from said subject, with a compound or agent capable of detecting the presence of Nm nucleic acid in the sample, and comparing the presence or absence of mRNA or DNA in the control sample with the presence of mRNA or DNA in the test sample. A control sample is optionally a portion of a test sample processed in parallel with the test sample. A control sample is optionally a purified, isolated, or otherwise processed nucleic acid sequence of known concentration optionally including at least a portion of the sodC sequence, where the nucleic acid sequence or portion thereof will hybridize under stringent conditions with a forward primer, a reverse primer, and, optionally, a probe. A control sample is used to produce a complementary amplification product produced either simultaneously with, or sequentially to the first amplification product produced from a target. The complementary amplification product is optionally detected by detecting a second detection signal by the same of a different method than that used to detect the first amplification product. Illustratively, a second amplification product is detected using a second probe of the same or of a different sequence than that use to detect the first amplification product. A second probe optionally has one or more labels that are the same or different than that of a first probe, when present. Illustratively, a control sample is subjected to the identical amplification conditions in the same or other parallel analysis, such as on the same instrument, as the test sample. If the test sample and the control sample are processed in different reaction chambers, the same probes with the same labels may be used.

Some embodiments include using a nucleic acid calibrator to produce a signal from a known quantity of sample molecule. A nucleic acid calibrator is optionally identical to or different from a target molecule. Amplification of a nucleic acid calibrator optionally produces a third detection signal, the presence of, intensity of, or size of is optionally compared to a first detection signal to quantify the amount of target, or amplification product in the test sample. Optionally, a plurality of nucleic acid calibrators are used. A plurality of nucleic acid calibrators are optionally of differing concentrations such as those suitable to produce a standard curve. The detection signal from the test sample is optionally compared to the standard curve to quantify the amount of amplification product or target in the test sample. A nucleic acid calibrator optionally includes a known amount of Neisseria meningitidis sodC nucleic acid sequence, or a portion of a Neisseria meningitidis sodC nucleic acid sequence.

The invention also encompasses kits for detecting the presence of Nm nucleic acids in a test sample. The kit, for example, includes a labeled compound or agent capable of detecting a nucleic acid molecule in a test sample and, in certain embodiments, for determining the quantity of Nm in the sample.

For oligonucleotide-based kits, the kit includes, for example: (1) an oligonucleotide, e.g., a detectably labeled oligonucleotide, which hybridizes to a nucleic acid sequence of Nm and/or (2) one or a pair of primers (one forward and one reverse) useful for amplifying a nucleic acid molecule containing at least a portion the Nm sequence such as the sodC sequence. The kit can also include, e.g., a buffering agent, a preservative, or a protein stabilizing agent. The kit can also include components necessary for detecting the detectable agent (e.g., an enzyme or a substrate). The kit can also contain a control sample or a series of control samples which is assayed and compared to the test sample contained. Each component of the kit is usually enclosed within an individual container and all of the various containers are usually enclosed within a single package along with instructions for use.

The processes are amenable to use for diagnosis of Nm infection or simple detection of the presence of Nm in a subject, such as insects, and any other organism capable of infection or transfection by or with Nm.

To increase confidence and to serve as an internal or external control, a purified solution containing Nm is used as a sample. Optionally, by amplification of a single sample with known quantities of Nm or of a set of samples representing a titration of Nm, the level of Nm in the unknown biological sample is determined, optionally as a control. Optionally, the purified and quantified Nm solution is analyzed in parallel with the unknown biological sample to reduce inter assay error or to serve as a standard curve for quantitation of unknown Nm in the test sample. Using purified and quantified Nm solution provides for a similar complete genetic base DNA strand for amplification.

In some embodiments, a subgenomic fragment is cloned into a plasmid for amplification, purification, and use as a quantitative comparator or nucleic acid calibrator. In a non-limiting example, a DNA subgenomic fragment of Nm is optionally amplified from a positive nasal swab using primers bracketing the RT-PCR target regions in sodC of Nm. It is appreciated that other sequences are similarly suitable for use as a quantitative control. The known concentration of the subgenomic fragment is used to create a standard curve for quantitative determinations and to access amplification efficiency.

Also provided is a kit for detecting or diagnosing Nm infection that contains reagents for the amplification, or direct detection of Nm or portions thereof in a sample. An exemplary kit optionally includes a forward and reverse primer pair, and a probe. In some embodiments, the forward and reverse primers have the oligonucleotide sequence SEQ ID NOs: 1 and 2 and a probe of the sequence SEQ ID NO 3. It is appreciated that a diagnostic kit optionally contains primers and probes that are the complements of SEQ ID NOs 1-3 or that hybridize with oligonucleotides SEQ ID NOs 1-3. It is further appreciated that a diagnostic kit optionally includes ancillary reagents such as buffers, solvents, thermostable polymerases, nucleotides, and other reagents necessary and recognized in the art for amplification and detection of Nm in a sample.

A kit for detection of Nm infection in a subject optionally contains reagents for PCR based detection of Nm genetic sequences, either structural or non-structural, and optionally for detection of antibodies directed to Nm proteins. The components of the kits are any of the reagents described above or other necessary and non-necessary reagents known in the art for solubilization, detection, washing, storage, or other need for in a diagnostic assay kit.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to samples derived from a human, a person having ordinary skill in the art recognizes that similar techniques and other techniques known in the art readily translate the examples to other organisms. Reagents illustrated herein are commonly cross reactive between mammalian species or alternative reagents with similar properties are commercially available, and a person of ordinary skill in the art readily understands where such reagents may be obtained.

Example 1

RT-PCR Assay Design

Control isolates for assay design and optimization are provided in Table 1:

TABLE 1

| Isolate | Used in This Study for | Received | From | Isolated From |
|---|---|---|---|---|
| M10481 | sodC sequencing | 2003 | North Carolina, USA | Eye |
| M16204 | sodC sequencing | 2007 | Connecticut, USA | Blood |
| M12221 | sodC sequencing | 2004 | Kenya | Unknown |
| M12746 | sodC sequencing | 2004 | Mali | CSF |
| M10697 | sodC sequencing | 2003 | Oregon, USA | Blood |
| M13169 | sodC sequencing | 2005 | Kentucky, USA | Blood |
| M12075 | sodC sequencing | 2001 | Canada | Blood |
| M11880 | sodC sequencing | 2004 | Georgia, USA | CSF |
| M12881 | sodC sequencing | 2004 | Hawaii, USA | Blood |
| M11701 | sodC sequencing | 2004 | South Africa | Unknown |
| M11986 | sodC sequencing | 2004 | California, USA | Blood |
| M14563 | sodC sequencing | 2006 | Ohio, USA | Blood |
| M15470 | sodC sequencing | 2006 | Colorado, USA | Blood |
| M10949 | sodC sequencing | 2003 | Pennsylvania, USA | Sputum |
| M5178 | Primer & probe optimization, standard curves | 1998 | Oregon, USA | Blood |

TABLE 1-continued

| Isolate | Used in This Study for | Received | From | Isolated From |
|---|---|---|---|---|
| M3702 | Standard curves | 1992 | CDC Reference Lab Surveillance Collection | Unknown |
| M18631 | Standard curves | 2009 | Oregon, USA | Blood |
| M18634 | Standard curves | 2009 | Oregon, USA | Blood |

[1]There is no Z or 29E PCR serogrouping assay currently in use in the CDC Meningitis Laboratory. However, these isolates tested negative by rt-PCR for serogroup A, B, C, W135, X, and Y genes.
[2]CTA sugar results Genomic DNA from each isolate was prepared for use in the various steps of assay design and optimization with the QIAamp DNA Mini Kit (QIAGEN, Valencia, Calif.) using Protocol C then quantified for use in standard curve experiments using a NanoDrop ND-1000 or 8000 spectrophotometer (Nanodrop Technologies, Wilmington, Del.). Preparation of DNA from bacterial isolates was performed as previously described by Mothershed, E A, et al., *J Clin Microbiol*, 2004; 42:320-328.

The sodC sequencing templates were prepared by conventional PCR using Expand High Fidelity Enzyme Mix (Roche Diagnostics GmbH) per the manufacturer's instructions and forward and reverse primers were designed based on a consensus of sodC from meningococcal strains Z2491 (nts 1521721-1522258), FAM18, and MC58 (respective GenBank accession numbers AL157959.1, AM421808.1, and AE002098.2), and provided as SEQ ID NOs: 4 and 5 respectively. DNA sequencing was performed using primers of SEQ ID NO: 4 (forward) and SEQ ID NO: 5 (reverse) at 400 nM and 100 nM respectively using the BigDye Terminator v3.1 Cycle Sequencing Kit (Applied Biosystems, Foster City, Calif.) and an ABI PRISM® 3130xl Genetic Analyzer (Applied Biosystems) and a consensus sequence was generated using Lasergene DNAStar v. 7 Program SeqMan.

Over the 439-473 out of 560 sodC nucleotides sequenced in these meningococcal isolates, these meningococcal sodC sequences are 99-100% were identical to each other and are only 81% identical to an *H. influenzae* (Hi) sodC consensus that was built using two sequences from GenBank (accession numbers M84012 and AF549211).

Primers for sodC specific amplification were designed based on the consensus sodC sequence to be located at positions not only containing at least three nucleotide differences between Nm and Hi, but also where sodC nucleotide sequence was conserved among the meningococcal isolates that were sequenced. The sodC consensus sequence was entered into Primer Express 3.0 (Applied Biosystems). Given that sodC was likely acquired by Nm via horizontal transfer from Hi, primers and a probe that differed by at least three nucleotides per oligo between Nm and Hi sodC were chosen. Primers and probes were analyzed for homology to other known sequences using the Basic Local Alignment Search Tool (BLAST). Altschul S F, et al., *J Mol Biol*, 1990; 215: 403-410. BLAST results showed that the primers of SEQ ID NOs: 1 and 2 had no homology that was over 78% nucleotide identity with any genes but meningococcal sodC. The only notable homology found for the probe of SEQ ID NO: 3 was a two-nucleotide difference with *H. parainfluenzae* sodC; the primers, however, showed no homology (less than two sequential nucleotides identical) to this gene.

To determine if the primers were capable of amplifying sodC, primers were tested for optimal concentration in triplicate or quadruplicate by RT-PCR in combinations of final concentrations of 100, 300, 600, and 900 nM; the probe was tested in triplicate at final concentrations of 50, 100, 200, and 300 nM. The amplified product is located at nt 1427446 in MC58 (GenBank accession number AE002098.2).

RT-PCR was performed as follows: A Stratagene Mx3005P (Agilent, La Jolla, Calif.) and QuantiTect SYBR Green Master Mix (QIAGEN) were used to optimize primer concentrations. Cycle parameters were 2 minutes at 50° C., 10 minutes at 95° C., and then 50×(15 seconds at 95° C. plus 1 minute at 60° C.). Product dissociation curves were generated using one round of the following cycle parameters at the end of the primer optimization run: one minute at 95° C., 30 seconds at 55° C., and 30 seconds at 95° C. For following studies, master mixes contained 4.5 µl sterile PCR grade water (Roche Diagnostics), 12.5 µl TaqMan®2×PCR Master Mix (Applied Biosystems), 300 nM forward primer (SEQ ID NO: 1), 600 nM reverse primer (SEQ ID NO: 2), 100 nM labeled probe (SEQ ID NO: 3; FAM-CATGATG-GCACAGCAACAAATCCTGTTT-BHQ1), and 2 µl template DNA per total reaction volume of 25 µl. With each reaction plate that was run, cell lysates from known Nm served as positive external amplification controls, while no-template controls (NTCs) served as negative external amplification controls. The primers of SEQ ID NOs: 1 and 2, along with the labeled probe of SEQ ID NO: 3 successfully amplified and detected sodC.

Example 2

Specificity and Characteristics of an Exemplary sodC RT-PCR Assay

The specificity of an RT-PCR based sodC assay for detecting only meningococci was determined using cell lysates from a total of 244 non-Nm isolates by the RT-PCR conditions of Example 1 using a forward primer of SEQ ID NO:1, a reverse primer of SEQ ID NO:2, and a probe of SEQ ID NO: 3. Each of the 244 non Nm isolates were negative by the assay RT-PCR method. None of 35 non-Nm from various sources and none of 209 non-meningococcal carriage study isolates were detected (100% specificity) as seen in Table 2.

Interestingly, the sodC assay identified one isolate, M16160, as Nm when other standard carriage study tests could not correctly resolve its species. It was originally identified as *N. polysaccharea/N.* spp. by NH strip, but upon re-investigation, did not grow at room temperature on chocolate agar, indicating that it is not *N. polysaccharea*. All 7 meningococcal housekeeping genes were readily amplified during MIST, suggesting that M16160 is indeed Nm (ST-7456, cc60), and again showing sodC to be a useful tool for definitive identification of carriage isolates.

The lower limit of detection was determined using standard curves generated by testing genomic DNA from four invasive meningococcal isolates with the sodC assay. LLDs at a $C_t$ value of 35 were found to be 39, 70, 101, and 82 genomes per reaction, yielding an average of 73 genomes detected per reaction. The average reaction efficiency was 100% and the average $R^2$ value was 0.9925.

Example 3

Sensitivity of the RT-PCR sodC Assay

The sensitivity of the RT-PCR assay of Example 1 using the primers of SEQ ID NOs: 1 and 2 and the probe of SEQ ID NO: 3 was determined using 626 cell lysates (listed in Dolan Thomas, J, et al., 2011, PLoS ONE 6(5): e19361, doi:10.1371/journal.pone.0019361) including lysates prepared from a temporally and geographically dispersed convenience sample of isolates from the CDC Meningitis Laboratory strain collection (received 1993-2008, n=106) and all isolates from a US carriage study (n=520) known to be Nm by SASG, RT-PCR serogrouping (Mothershed, et al.), NH strips (bioMérieux® sa), and Cystine Trypticase Agar (CTA) sugars (Remel). To further confirm identification, multilocus sequence typing (MLST) was performed on all U.S. carriage study and ctrA-negative NG isolates.

All isolates were positive for sodC using these primers and probe, including 26 ctrA-negative NG isolates, with a median $C_t$ value of 19.7, mean of 19.9±1.9, and range of 16.4 to 26.0.

Additional samples from two U.S. carriage studies were also tested. 518/520 (99.6%) of meningococcal carriage isolates from the studies were positive for sodC (median $C_t$ 16.9, mean 17.0±1.5, and range 13.5 to 29.3), while ctrA detected only 368/520 (70.8%) of these isolates (median $C_t$ 19.0, mean 19.2±2.7, and range 13.5 to 34.0). The two sodC-negative isolates carrying Nm were SASG NG, ctrA-negative but were confirmed to be Nm ST-1117 and ST-4788, both cc1117; both were isolated from the same study participant at different time points. Therefore, 176/178 (98.9%) SASG NG, ctrA-negative invasive and non-invasive Nm isolates were sodC positive by this assay. Four sodC-negative carriage study isolates that were identified as Nm by conventional methods were re-investigated and shown to actually be non-Nm.

Example 4

Assay for Presence of Nm in Biological Samples from Clinical Sources

The ability of the sodC assay of Example 2 to detect Nm was assessed and was compared to ctrA as the target gene using extracted DNA from 120 Turkish cerebrospinal fluid (CSF) specimens and 37 U.S. clinical specimens.

For the clinical samples, CSF specimens from pediatric meningitis patients were cultured as soon as possible after collection. Specimens that were culture-negative were sent to CDC on ice for detection of meningitis etiology by the Marmara University School of Medicine in Istanbul, Turkey, and came from patients who met the case definition for purulent meningitis [leukocytosis (>100 cells/mm$^3$) and either elevated protein (>100 mg/dl) or decreased glucose (<40 mg/dl)]. DNA extraction was performed as previously described for clinical specimens with the QIAamp DNA Mini Kit (QIAGEN, Valencia, Calif.) using Protocol C. After DNA extraction and real-time PCR testing of all specimens for ctrA of Nm as described by Mothershed E A, et al., *J Clin Microbiol*, 2004; 42:320-328, lytA of *S. pneumoniae* as described by Carvalho M da G, et al., *J Clin Microbiol*, 2007; 45:2460-2466, and bexA and/or bcs2 of Hi, the subset of specimens chosen to test the sodC assay (n=120) were either (1) positive for ctrA (n=12) or (2) ctrA$^-$ lytA$^-$ bexA/bcs2$^-$ (n=108).

37 U.S. clinical specimens were referred to CDC for detection or confirmation of bacterial meningitis etiology from January to June 2009, including CSF (n=21), whole blood (n=6), serum (n=6), and tissues (n=4).

The RT-PCR assay of Example 1 was used to examine each of the samples for the presence or absence of Nm. Results are illustrated in Table 3. Briefly, screening for ctrA detected Nm in 21/157 (13.4%) specimens (20 CSF and 1 blood), while the assay of Example 2 for sodC was positive for those 21 plus four additional CSF specimens (25/157, 15.9%). Therefore, the RT-PCR assay for sodC was 100% (95% confidence interval [CI]: 84-100%) sensitive compared to ctrA at detection of Nm from these clinical specimens. The $C_t$ values for the four ctrA-negative, sodC-positive CSF extractions averaged 40.4 for ctrA while their sodC $C_t$ values averaged 32.0.

One ctrA-negative, sodC-positive CSF specimen was Nm culture-positive (1/157, 0.6%); the remaining specimens were either culture-negative (139/157) or culture was not attempted or not reported (17/157). Therefore, sodC was 88% (95% CI: 82-93%) specific compared to culture at detection of Nm from the clinical specimens for which culture was attempted.

Example 5

Detection of Nm in Carriage Specimens

The assay of Example 1 was also used to screen for the presence or absence of Nm in carriage specimens. The carriage specimens were obtained from three carriage studies. In a first study from Goiania, Brazil, nasopharyngeal (NP) swabs (n=223) were obtained from 154 children (ranging from 2-163 months of age) attending two daycare centers, 59 adult contacts of the attendees, and 10 daycare workers. The specimens were placed into skim milk-tryptone-glucose-glycerine (STGG) transport medium and sent immediately to the Applied Microbiology Laboratory of Federal University of Goias in Brazil for processing. The vials were then kept frozen during transport to CDC, where DNA extractions and RT-PCR were performed.

Second, 291 posterior NP swab specimens were collected from a random sample of children 6 to 59 months of age who presented to the Emergency Department at CHOA at Egleston from March to August, 2009. Each swab specimen was immediately placed into 1 ml STGG. Specimens were transported at room temperature to the clinical microbiology laboratory within 12 hours of collection for storage at −80° C. until processing. An aliquot of the STGG from each specimen was transported on dry ice to the CDC Meningitis Laboratory, where DNA extractions and RT-PCR were performed.

Third, a total of 33 NP swabs and 35 nasal washes (NWs) were taken from 24 participants ages 21-57 years during ≤7 visits in a Spring 2009 study conducted in the NIHR Biomedical Research Centre in Microbial Diseases at the Liverpool School of Tropical Medicine, Liverpool, United Kingdom (UK). Swab specimens were collected as previously described (O'Brien K L, and Nohynek H, Pediatr Infect Dis J, 2003; 22:e1-11) with some modifications and placed directly into 1 ml STGG, then transported to the laboratory on wet ice for culture and processing. 900 µl of each specimen was frozen at −80° C. for subsequent DNA extraction and rt-PCR in Liverpool.

For CSF specimens and the Brazilian NP swab eluates, DNA extraction was conducted as previously described for clinical specimens. O'Brien K L, et al., *J Clin Microbiol*, 2001; 39:1021-1024. DNA extractions were performed on the CHOA carriage study NP swab eluates using the MagNA Pure LC instrument and the DNA Isolation Kit III (Bacteria, Fungi) per the manufacturer's instructions (Roche Diagnostics GmbH, Mannheim, Germany). DNA was extracted from the UK NP and NW specimens using the QIAsymphony SP System and the QIAsymphony Virus/Bacteria Midi Kit (QIAGEN Inc., UK) according to the manufacturer's instructions. All extracted DNA was stored at −20° C.

Results from all three carriage studies are summarized in Table 4. None (0/223, 0%) of the Brazilian NP swab eluate extractions tested at CDC were ctrA-positive, while 3 (3/223, 1.3%) were sodC-positive, yielding $C_t$ values of 29.1, 26.2, and 25.5. The ctrA-negative, sodC-positive specimens were negative for serogroups A, B, C, W135, X, and Y by rt-PCR. In the 1/3 ctrA-negative, sodC-positive specimen that had a sufficient amount of extraction volume remaining, MLST confirmed the presence of meningococcal DNA (ST-823, cc198). All 23 Hi culture-positive Brazilian specimens were ctrA- and sodC-negative.

All (291/291, 100%) NP swab eluate extractions from the Georgia CHOA carriage study were ctrA-negative and sodC-negative, as expected, since no Nm was cultured. These specimens were, however, culture-positive for *N.* spp. (n=3), *N. polysaccharea* (n=1), *M. catarrhalis* (n=8), *H. parainfluenzae* (n=9), *H. haemolyticus* (n=1), and Hi (n=76), further demonstrating the specificity of sodC as a target for the presence of Nm in samples.

*S. aureus* (n=17), alpha-hemolytic streptococci (n=18), *M. catarrhalis* (n=5), diptheroids (n=10), *N. polysaccharea* (n=1), *N. cinerea* (n=2), and *N. meningitidis* (n=1) were cultured from the 68 UK carriage study specimens. The Nm culture-positive NW was ctrA-positive and sodC-positive. sodC and ctrA were negative for all of the non-Nm culture-positive specimens except one ctrA-positive, sodC-positive NW that grew *N. cinerea* and alpha-hemolytic streptococci. 1/33 (3%) NP swab eluate extractions from the UK carriage study were ctrA-positive, 0/33 were sodC-positive, and 0/33 were Nm culture-positive. 3/35 (8.6%) NW extractions were ctrA-positive, 2/35 (5.7%) were also sodC-positive; of these, one (1/35, 2.9%) ctrA-positive, sodC-positive NW was Nm culture-positive. The ctrA-positive, sodC-negative NP specimen (average ctrA $C_t$ 35.0±0.3, average sodC $C_t$ 37.8±0.8) and the ctrA-positive, sodC-negative NW (average ctrA $C_t$ value of 34.3±0.2 and an average sodC $C_t$ value of 35.1±0.2) were both from patient 8, visit 3; this patient had the Nm-positive culture at visit 1 and the *N. cinerea*-positive culture at visit 2.

Example 6

Detection of Nm by PCR/LC/MS

The isolates of Table 1 are each rescreened using PCR amplification with parameters similar to the RT-PCR assay of Example 1. Genomic DNA is subjected to cycle parameters of 2 minutes at 50° C., 10 minutes at 95° C., and then 50×(15 seconds at 95° C. plus 1 minute at 60° C.). For each amplification reaction, master mixes contain 4.5 µl sterile PCR grade water (Roche Diagnostics), 12.5 µl TaqMan®2× PCR Master Mix (Applied Biosystems), 300 nM forward primer (SEQ ID NO: 1), 600 nM reverse primer (SEQ ID NO: 2), and 2 µl template DNA per total reaction volume of 25 µl.

The reaction products are subjected to analyses by electrospray ionization mass spectrometry substantially as described by Naito, Y, et al., *Rapid Communications in Mass Spectrometry*, 1995; 9:1484-1486; or Wunschel D S, et al., *Rapid Commun Mass Spectrom*. 1996; 10(1):29-35. Each of the reaction products from the PCR reactions are successfully and rapidly detected.

Example 7

Detection of Nm by PCR/Gel Electrophoresis

The isolates of Table 1 are each rescreened using PCR amplification with parameters similar to the RT-PCR assay of Example 1. Genomic DNA is subjected to cycle parameters of 2 minutes at 50° C., 10 minutes at 95° C., and then 50×(15 seconds at 95° C. plus 1 minute at 60° C.). For each amplification reaction, master mixes contain 4.5 µl sterile PCR grade water (Roche Diagnostics), 12.5 µl TaqMan®2× PCR Master Mix (Applied Biosystems), 300 nM forward primer (SEQ ID NO: 1), 600 nM reverse primer (SEQ ID NO: 2), 100 nM labeled probe (SEQ ID NO: 3; Alexa 488-5'-CATGATGGCACAGCAACAAATCCTGTTT-3'), and 2 µl template DNA per total reaction volume of 25 µl.

The amplified reaction products are separated by gel electrophoresis and detected by fluorescent imaging. Each of the isolates show detectable amplified sodC DNA.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Additional protocols such as PCR Protocols can be found in A Guide to Methods and Applications Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," Methods in Enzymology vol. 182, and other volumes in this series; Current Protocols in Protein Science, John Wiley and Sons, New York, N.Y.; and manufacturer's literature on use of protein purification products known to those of skill in the art.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

REFERENCE LIST 1. 2009. Pediatric bacterial meningitis surveillance—African region, 2002-2008. MMWR Morb Mortal Wkly Rep 58:493-7.
2. Altschul, S. F., et al, J Mol Biol, 1990; 215:403-10.
3. Benson, D. A., et al., Nucleic Acids Res, 2009; 37:D26-31.

4. Bingen, E., et al., Eur J Clin Microbiol Infect Dis, 1990; 9:278-81.
5. Carvalho Mda, G., et al. J Clin Microbiol, 2007; 45:2460-6.
6. Cavrini, F., et al, J Clin Microbiol, 2010; 48:3016-8.
7. Chiba, N., et al., J Infect Chemother, 2009; 15:92-8.
8. Clark, T. A., 2008; Presented at the 16th International Pathogenic Neisseria Conference, Rotterdam, The Netherlands, Sep. 7-12, 2008.
9. Claus, H., et al, Microbiology, 2002; 148:1813-9.
10. Corless, C. E., et al., J Clin Microbiol, 2001; 39:1553-8.
11. Deutch, S., et al, Scand J Infect Dis, 2008; 40:607-14.
12. Dolan-Livengood, J. M., et al., J Infect Dis, 2003; 187:1616-28.
13. Fung, W. W., et al., J Clin Microbiol, 2006; 44:4222-6.
14. Gurley, E. S., et al., Am J Trop Med Hyg, 2009; 81:475-83.
15. Hedberg, S. T., et al., APMIS; 2009; 117:856-60.
16. Janda, W. M. a. C. A. G. 2007. *Neisseria*, p. 601-620. In P. R. Murray (ed.), Manual of Clinical Microbiology 9th ed, vol. 1. ASM Press, Washington, D.C.
17. Jordens, J. Z., and J. E. Heckels., J Med Microbiol, 2005; 54:463-6.
18. Jordens, J. Z., et al., J Clin Microbiol, 2002; 40:75-9.
19. Katz, L. S., et al., Nucleic Acids Res, 2009; 37:W606-11.
20. Kellerman, S. E., et al., J Infect Dis, 2002; 186:40-8.
21. Kroll, J. S., et al., Proc Natl Acad Sci USA, 1998; 95:12381-5.
22. La Scolea, L. J., Jr., and D. Dryja. J Clin Microbial, 1984; 19:187-90.
23. Langford, P. R., et al., J Gen Microbiol, 1992; 138:517-22.
24. Maiden, M. C., Proc Natl Acad Sci USA, 1998; 95:3140-5.
25. McCrea, K. W., et al., J Clin Microbial, 2010; 48:714-9
26. Mothershed, E. A., et al., J Clin Microbiol, 2004; 42:320-8.
27. Murray, P. R., and E. J. Baron. 2007. Manual of clinical microbiology, 9th ed. ASM Press, Washington, D.C.
28. Naclerio, R. M., et al., Am Rev Respir Dis, 1983; 128:597-602.
29. O'Brien, K. L., et al., J Clin Microbiol, 2001; 39:1021-4.
30. O'Brien, K. L., and H. Nohynek. Pediatr Infect Dis J, 2003; 22:e1-11.
31. Popovic, T., G. Ajello, and R. Facklam. 1999. Laboratory Manual for the Diagnosis of Meningitis Caused by *Neisseria meningitidis, Streptococcus pneumoniae* and *Haemophilus influenzae*. World Health Organization.
32. Sadler, F., et al., Epidemiol Infect, 2003; 130:59-70.
33. Staden, R., Mol Biotechnol, 1996; 5:233-41.
34. Staquet, P., et al., Intensive Care Med, 2007; 33:1168-72.
35. Swartley, J. S., et al., Proc Natl Acad Sci USA, 1997; 94:271-6.
36. Taha, M. K. et al, J Clin Microbiol, 2000; 38:855-7.
37. Taha, M. K., et al., J Clin Microbiol, 2005; 43:144-9.
38. Tettelin, H., et al., Science, 2000; 287:1809-15.
39. Tseng, H. J., et al., Mol Microbiol, 2004; 40:1175-86.
40. Uria, M. J., et al., J Exp Med, 2008; 205:1423-34.
41. van der Ende, A., et al., J Clin Microbiol, 1995; 33:3326-7.
42. Van Gastel, et al., Eur J Clin Microbiol Infect Dis, 2007; 26:651-3.
43. Wang, X., C. et al., 2009. Protein D gene as a target for detection of *Haemophilus influenzae*. Presented at the 109th General Meeting of the American Society for Microbiology, Philadelphia, Pa.
44. Wilks, K. E., et al., Infect Immun, 1998; 66:213-7.
45. Zhu, B. Q., et al., Zhonghua Liu Xing Bing Xue Za Zhi, 2008; 29:360-4.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

TABLE 2

| Organism[1] | n | sodC+ |
|---|---|---|
| M. catarrhalis | 22 | 0 |
| H. aphrophilus/paraphrophilus | 2 | 0 |
| H. aphrophilus | 1 | 0 |
| H. influenzae biogroup aegyptius | 1 | 0 |
| H. influenzae serotype a | 1 | 0 |
| H. influenzae serotype b | 1 | 0 |
| H. influenzae serotype c | 1 | 0 |
| H. influenzae serotype d | 1 | 0 |
| H. influenzae serotype e | 2 | 0 |
| H. influenzae serotype f | 1 | 0 |
| H. influenzae nontypeable (NTHi) | 81 | 0 |
| H. parainfluenzae | 10 | 0 |
| H. haemolyticus | 1 | 0 |
| N. lactamica | 93 | 0 |
| N. spp. | 3 | 0 |
| N. polysaccharea | 1 | 0 |
| N. cinerea | 2 | 0 |
| N. subflava | 1 | 0 |
| N. sicca | 2 | 0 |
| N. gonorrhoeae | 5 | 0 |
| E. coli K1 | 2 | 0 |
| C. neoformans | 1 | 0 |
| S. aureus | 1 | 0 |
| S. pneumoniae | 1 | 0 |
| L. monocytogenes | 1 | 0 |
| A. pleuropneumoniae | 1 | 0 |
| S. choleraesuis | 1 | 0 |
| S. agalactiae | 1 | 0 |
| P. aeruginosa | 1 | 0 |
| C. diptheriae | 1 | 0 |
| B. pertussis | 1 | 0 |
| Total | 244 | 0 |

[1] 92 N. lactamica, 4 N. gonorrhoeae, 19 M. catarrhalis, and 2 H. spp. from this panel were collected in a Georgia Nm carriage study (8). 3 N. spp., 1 N. polysaccharea, 2 M. catarrhalis, 9 H. parainfluenzae, and 76 NTHi and 1 Hie were collected in a Georgia Hib carriage study (Sharma, et al., in preparation)

TABLE 3

| Specimen | Total n | n sodC+ | % sodC+ | 95% CI | n ctrA+ | % ctrA+ | 95% CI[1] | n Nm Culture Positive[2] | % Culture Positive | 95% CI |
|---|---|---|---|---|---|---|---|---|---|---|
| CSF | 141 | 24 | 17.0 | 11% to 24% | 20 | 14.2 | 9% to 21% | 1 | 0.7 | 0% to 4% |
| Blood | 6 | 1 | 16.7 | 0% to 64% | 1 | 16.7 | 0% to 64% | 0 | 0.0 | 0% to 46% |

TABLE 3-continued

| Specimen | Total n | n sodC+ | % sodC+ | 95% CI | n ctrA+ | % ctrA+ | 95% CI[1] | n Nm Culture Positive[2] | % Culture Positive | 95% CI |
|---|---|---|---|---|---|---|---|---|---|---|
| Serum | 6 | 0 | 0.0 | 0% to 46% | 0 | 0.0 | 0% to 46% | 0 | 0.0 | 0% to 46% |
| Body Tissue | 4 | 0 | 0.0 | 0% to 60% | 0 | 0.0 | 0% to 60% | 0 | 0.0 | 0% to 60% |
| Total | 157 | 25 | 15.9 | n/a | 21 | 13.4 | n/a[3] | 1 | 0.6 | n/a |

[1]Exact binomial 95% confidence interval
[2]Culture was attempted for all 120 Turkey CSF specimens. With the exception of the one ctrA-negative, sod/C-positive U.S. CSF specimen that was culture-positive, culture was either not attempted, not reported, or in one case, the isolate was nonviable two times for the other 36 U.S. clinical specimens.
[3]n/a, not applicable

TABLE 4

| Specimen | Total n | n sodC+ | % sodC+ | 95% CI[1] | n ctrA+ | % ctrA+ | 95% CI | n Nm Culture Positive | % Culture Positive | 95% CI |
|---|---|---|---|---|---|---|---|---|---|---|
| NP swab eluate | 547 | 3 | 0.5 | 0% to 2% | 1[2] | 0.2 | 0% to 1% | 0 | 0.0 | 0% to 1% |
| Nasal wash | 35 | 2[3] | 5.7 | 1% to 19% | 3 | 8.6 | 2% to 23% | 1[4] | 2.9 | 0% to 15% |
| Total | 582 | 5 | 0.9 | n/a[5] | 4 | 0.7 | n/a | 1 | 0.2 | n/a |

[1]Exact binomial 95% confidence interval
[2]This ctrA-positive NP swab eluate was sodC-negative.
[3]Both of these soc/C-positive NP swab eluates were ctrA-positive.
[4]This Nm culture-positive NW was ctrA-positive, sodC-positive.
[5]n/a, not applicable

The invention claimed is:

1. A process of detecting *Neisseria meningitidis* in a sample comprising:
   producing an amplification product using a polymerase chain reaction by amplifying a *Neisseria meningitidis* nucleotide sequence using a forward primer that hybridizes to a region within the sodC gene or sodC mRNA of *Neisseria meningitidis*, and a reverse primer that hybridizes to a region within the sodC gene or sodC mRNA of *Neisseria meningitidis*, under conditions suitable for a polymerase chain reaction, wherein said forward primer is SEQ ID NO: 1 and said reverse primer is SEQ ID NO: 2; and
   detecting said amplification product to detect the *Neisseria meningitidis* in said sample.

2. The process of claim 1 wherein said step of detecting comprises a hybridizing to said amplification product a probe of SEQ ID NO: 3 to produce a first detection signal.

3. The process of claim 2 wherein hybridizing said probe is under conditions suitable for a polymerase chain reaction; and further
   detecting said first detection signal from said probe hybridized to said amplification product.

4. The process of claim 1 wherein said step of producing is in a sample obtained from a subject suspected of having a *Neisseria meningitidis* infection, and said step of detecting diagnoses said *Neisseria meningitidis* infection in a subject.

5. The process of claim 2 further comprising comparing said first detection signal to a second detection signal, wherein said second detection signal results from detection of a complementary amplification product produced from a control sample.

6. The process of claim 5 wherein said second detection signal is generated in parallel with said first detection signal.

7. The process of claim 5, wherein said complementary amplification product is generated by PCR amplification of a purified *Neisseria meningitidis* or portion thereof.

8. The process of claim 5, wherein said first detection signal is compared to a third detection signal from a nucleic acid calibrator extracted in parallel to said sample.

9. The process of claim 8, wherein said nucleic acid calibrator comprises a known amount of *Neisseria meningitidis* sodC nucleic acid sequence and a known amount of a medium.

10. The process of claim 1 wherein said step of detecting is by gel electrophoresis, Southern blotting, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time PCR, nucleotide sequencing, or combinations thereof.

11. The process of claim 1 further comprising diagnosing or confirming a diagnosis of the presence or absence of infection by *Neisseria meningitidis* in a subject by detecting the presence or absence of said amplification product produced from said sodC gene or said sodC mRNA.

* * * * *

SEQUENCE LISTING

<160> NUMBER OF SEQ ID NOS: 5

<210> SEQ ID NO 1
<211> LENGTH: 25
<212> TYPE: DNA
<213> ORGANISM: Neisseria meningitidis
<220> FEATURE:
<221> NAME/KEY: misc_feature
<223> OTHER INFORMATION: SodC rt-pcr fwd primer

<400> SEQUENCE: 1
gcacacttag gtgatttacc tgcat                                         25

<210> SEQ ID NO 2
<211> LENGTH: 23
<212> TYPE: DNA
<213> ORGANISM: Neisseria meningitidis
<220> FEATURE:
<221> NAME/KEY: misc_feature
<223> OTHER INFORMATION: SodC rt-pcr rev primer

<400> SEQUENCE: 2
ccacccgtgt ggatcataat aga                                           23

<210> SEQ ID NO 3
<211> LENGTH: 28
<212> TYPE: DNA
<213> ORGANISM: Neisseria meningitidis
<220> FEATURE:
<221> NAME/KEY: misc_feature
<223> OTHER INFORMATION: rt-pcr probe

<400> SEQUENCE: 3
catgatggca cagcaacaaa tcctgttt                                      28

<210> SEQ ID NO 4
<211> LENGTH: 22
<212> TYPE: DNA
<213> ORGANISM: Neisseria meningitidis

```
<220> FEATURE:
<221> NAME/KEY: misc_feature
<223> OTHER INFORMATION: sequencing fwd primer

<400> SEQUENCE: 4
ccttattagc actagcggtt ag                                              22

<210> SEQ ID NO 5
<211> LENGTH: 22
<212> TYPE: DNA
<213> ORGANISM: Neisseria meningitidis
<220> FEATURE:
<221> NAME/KEY: misc_feature
<223> OTHER INFORMATION: sequencing rev primer

<400> SEQUENCE: 5
ccggtcatct tttatgctcc aa                                              22
```